(12) United States Patent
Holzer

(10) Patent No.: US 7,419,508 B2
(45) Date of Patent: Sep. 2, 2008

(54) LIGHT PROSTHESIS

(75) Inventor: Heide-Marie Holzer, Klagenfurt (AT)

(73) Assignees: Austria Wirtschaftsservice Gesellschaft Mit Beschrankter Haftung, Vienna (AT); Gerold Holzer, Klagenfurt (AT)

( * ) Notice: Subject to any disclaimer, the term of this patent is extended or adjusted under 35 U.S.C. 154(b) by 0 days.

(21) Appl. No.: 10/565,444

(22) PCT Filed: Jul. 23, 2004

(86) PCT No.: PCT/AT2004/000266

§ 371 (c)(1),
(2), (4) Date: Jan. 20, 2006

(87) PCT Pub. No.: WO2005/009304

PCT Pub. Date: Feb. 3, 2005

(65) Prior Publication Data

US 2006/0173553 A1  Aug. 3, 2006

(30) Foreign Application Priority Data

Jul. 25, 2003 (AT) .............................. A 1183/2003

(51) Int. Cl.
*A61F 2/60* (2006.01)
(52) U.S. Cl. .......................................... 623/33; 623/27
(58) Field of Classification Search ............ 623/27–65; 602/23–27, 62–63
See application file for complete search history.

(56) References Cited

U.S. PATENT DOCUMENTS

| 1,512,563 A | 10/1924 | Roberts |
| 1,525,633 A | 2/1925 | Witmyer |
| 1,649,773 A | 11/1927 | Witmyer |
| 4,468,821 A | 9/1984 | Saunders |
| 5,152,800 A | 10/1992 | Rothschild et al. |
| 5,651,792 A * | 7/1997 | Telikicherla .................. 623/36 |
| 5,728,165 A | 3/1998 | Brown, Sr. |
| 2002/0165619 A1 * | 11/2002 | Hellberg ....................... 623/36 |

FOREIGN PATENT DOCUMENTS

| EP | 0 151 834 A1 | 8/1985 |
| GB | 2 064 331 A | 6/1981 |

* cited by examiner

*Primary Examiner*—Bruce E. Snow
(74) *Attorney, Agent, or Firm*—Chalker Flores, LLP; Edwin Flores; Daniel J. Chalker

(57) ABSTRACT

The invention relates to a light prosthesis as a purely optical substitute for a missing limb, including a shaped body (1) for replacing the missing limb as naturally as possible and a socket (2) for connecting the prosthesis to the stump (3) of the missing limb. In order to provide such a prosthesis for temporary or permanent use without having to fulfill any functionality, thus being suitable also for elderly patients, it is contemplated that the shaped body (1) is made of a light synthetic material, and that the periphery of the socket (2) for connecting the prosthesis to the stump (3) is variable in a manner known per se. The shaped body (1) may, in particular, also be made of an elastic, air-tight synthetic material (9) and include at least one valve (10) for inflating the shaped body (1).

7 Claims, 2 Drawing Sheets

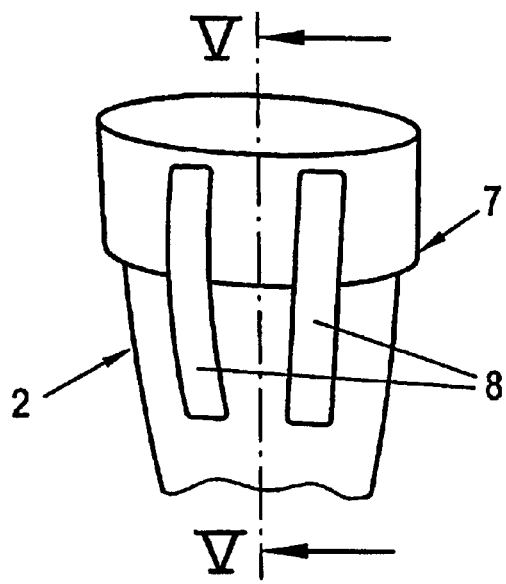
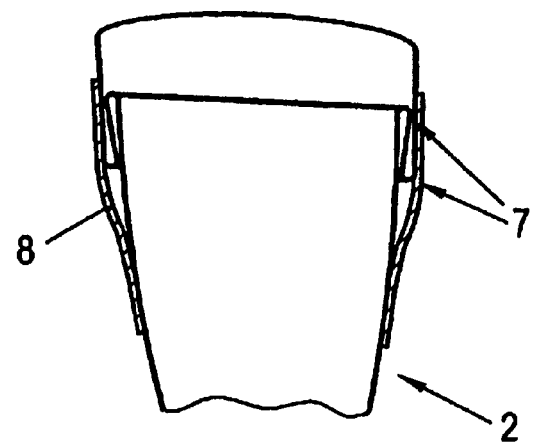
FIG. 4  FIG. 5
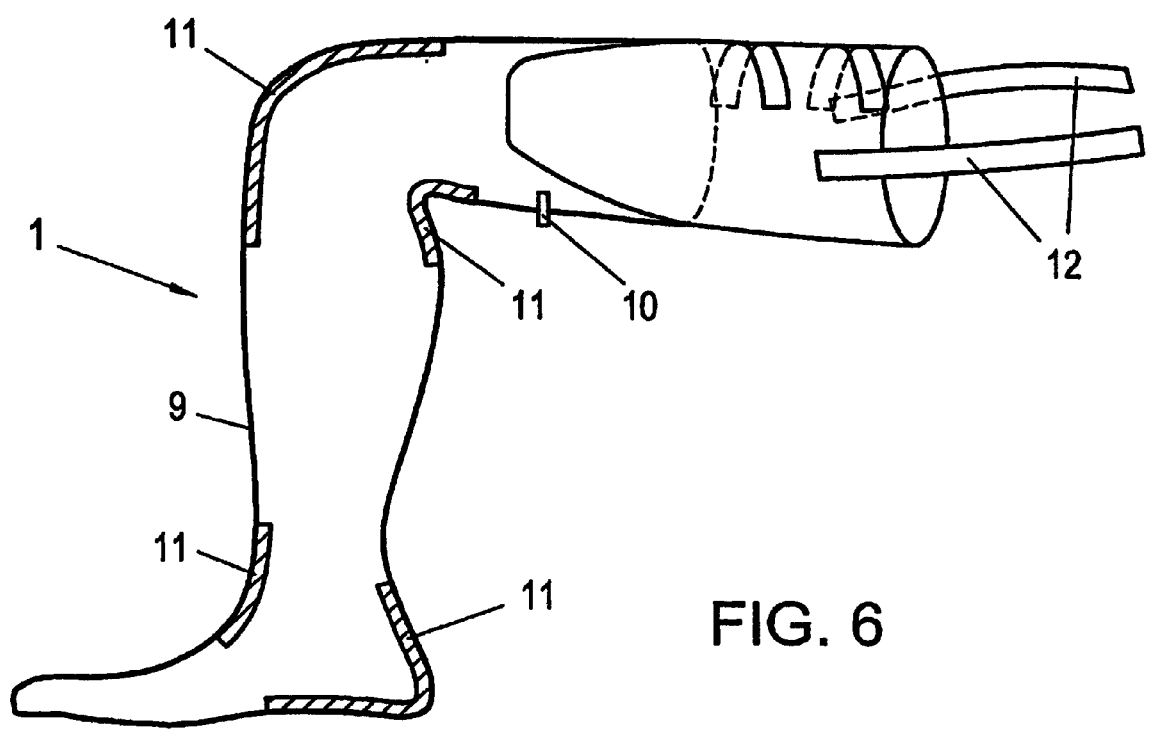
FIG. 6

LIGHT PROSTHESIS

The invention relates to a light prosthesis as a purely optical substitute for a missing limb, and including a shaped body for replacing the missing limb and a socket for connecting the prosthesis to the stump of the missing limb.

The invention merely serves as an optical limb substitute for the temporary or permanent assistance of all kinds of amputations of the upper and lower limbs. The present prosthesis is not aimed to provide stability or functionality. This means that the prosthesis is not intended to be used for walking or gripping, but merely as an optical substitute that replaces the missing limb as naturally as possible.

Elderly patients, in particular, after amputations are unable to handle prostheses that allow for walking or gripping. The reasons for this, on the one hand, reside in the bad physical conditions of elderly patients and, on the other hand, in poorer wound healing, which does not allow for the use of normal prostheses. Nevertheless, missing limbs also constitute mental problems in elderly patients, which is why there is a need for cosmetic prostheses.

In addition to a number of prostheses fulfilling walking and gripping functions, there have also existed prostheses for temporary use.

EP 0 151 834 A1, for instance, describes a leg prosthesis to be particularly used for bathing purposes, which is comprised of a relatively solid socket and inwardly provided with several inflatable air chambers. The foot region offers a relatively large supporting surface including a stiff sole. The air chamber between the sole and the stump of the missing limb assumes a certain stability such that stepping on the artificial limb is feasible at least to some degree. If the prosthesis is not used, it can be folded for storage or transportation. In order to achieve the required stability, the prosthesis widens towards the foot, which is not in correspondence with the natural shape of a leg such that a prosthesis of this kind cannot serve as an optical substitute.

GB 2 064 331 A describes an inflatable prosthesis for use, in particular, immediately after an amputation or after a very long use of a conventional prosthesis. In order to enable the examination of the stump of the missing limb even with the attached prosthesis, the latter is preferably made of a transparent material. In order to achieve a certain stability, the prosthesis is made of a relatively thick material and composed of two layers with several air chambers being formed between said two layers. The prosthesis is designed to taper downwardly, ending in a knob-like element. Also that prosthesis is not suitable as an optical substitute for a missing limb.

Finally, U.S. Pat. No. 3,889,301 A discloses a leg prosthesis in which the socket for the stump of the missing limb is provided with an inflatable layer. Such prostheses are used for therapeutic purposes of new amputees. The lower portion of the prosthesis comprises a stem and a foot replacement that does not correspond with the shape of a natural leg.

U.S. Pat. No. 4,790,855 A relates to an elastic supporting element for fastening a leg prosthesis above the knee after a leg amputation. The element essentially consists of a part made of a flexible, elastic material, which is connected to the stump as well as to the waist, preferably by Velcro fasteners. The periphery of the supporting elements can, thus, be adapted to the respective periphery of the stump. There is no indication as to the nature of the prosthesis itself, nor of the socket used to connect the prosthesis with the stump.

EP 0 806 193 A1 discloses a leg prosthesis which includes a special, extremely elastic sleeve as a socket for connecting the prosthesis to the stump. The sleeve is pulled both over the stump and over the proximal end of the prosthesis, thus providing the safe support of the prosthesis on the stump. The handleability of such a sleeve, however, is relatively complex.

The object of the present invention, therefore, resides in providing an initially mentioned prosthesis which is to be connected to the stump of the missing limb in a manner as simple as possible, offering a structure as light-weight and simple as possible. The prosthesis need not fulfill a walking or gripping function, but merely serves as an optical substitute for a missing limb. Moreover, the prosthesis according to the invention is to be applicable to as wide a spectrum of differently sized limbs as possible without requiring special designs, which are expensive and complex. The production costs of the prosthesis are to be as low as possible for as wide an application as possible.

The object according to the invention is achieved in that the shaped body is made of a light synthetic material, and that the periphery of the socket for connecting the prosthesis to the stump is variable in a manner known per se. Such a prosthesis in which the shaped body is made of a light synthetic material can be produced in a relatively easy and cost-effective manner and has low weight. On account of the variable periphery of the socket for connecting the prosthesis to the stump of the missing limb, the prosthesis can be used for different stump dimensions. The described prosthesis may, thus, be used as an optical substitute for the missing limb even of elderly patients who are no longer able to wear functional prostheses. It is, thus, for instance, feasible for diabetics, who frequently suffer amputations of their upper and lower limbs at high ages as late symptoms of their disease, to wear such prostheses. Leg amputees may, for instance, wear such prostheses while sitting in their wheelchairs, so that the missing limb will not, or not immediately, be apparent. The shaped body may, for instance, be hollow or made of a light material, for instance Styropore, and preferably include a cover of a resistant plastic.

The variability of the periphery of the socket used to connect the prosthesis to the stump may be realized in that the socket is made of an elastic material at least over a partial region of its periphery. This constitutes an option for obtaining a variable periphery to be realized in a particularly simple manner.

According to another characteristic feature of the invention, it is provided that the socket includes quick-acting closures, for instance Velcro fasteners, to fix the stump. The application of the prosthesis can, thus, be carried out in a particularly quick and simple manner by elderly patients.

In an advantageous manner, the length too of the socket is variable such that the prostheses can also be used by differently tall patients having differently long limbs.

The variability of the length of the socket may be provided in that the socket is made of an elastic material at least over a partial region of its length, and that the elastic material forms at least one pleat in said partial region to achieve a change in the length of the socket. The socket in a partial region may, in particular, be designed with an overlay formed by two pleats, said overlay being adapted to the length of the stump and the length of the limb.

In an advantageous manner, the at least one pleat is fixed by quick-acting closures, in particular Velcro fasteners. The prosthesis can, thus, be rapidly and readily fixed in the desired length.

The shaped body of the prosthesis for the optical substitution of missing limbs may also include a joint or several joints to replace the joint(s) of the missing limb. The functionality of this joint, however, is to be limited to what is absolutely necessary. This means, for instance, that in the event of a leg prosthesis a certain flexion of the knee joint is to be enabled, whereas no functionality of the foot joint is usually required.

In an advantageous manner, the shaped body of the prosthesis is made of an elastic, air-tight synthetic material and comprises at least one valve for inflating said shaped body. Thus, an inflatable prosthesis can be realized, which is particularly simple and cost-effective to produce. Due to the socket designed according to the invention, it is not necessary to provide a custom-made prosthesis for every patient, which would increase production costs.

The shaped body may comprise several interconnected air chambers. By the special arrangement of the air chambers, it is feasible to perfectly imitate the natural shape of the missing limb.

Reinforcing layers of synthetic material may be provided in partial regions on the inner side of the shaped body. They can serve to form joints or reinforce stressed zones, for instance the heel zone, of the foot over which the shoe is slipped.

The surface of the shaped body is suitably formed to imitate the skin of the missing limb by an appropriate colouration and surface structure.

In the event of particularly high amputations with, for instance, partial pelvectomies, it is advantageous if the prosthesis comprises fastening strips to secure the prosthesis to the patient's body.

The present invention will be explained in more detail by way of the attached drawings schematically illustrating exemplary embodiments of the invention.

Therein:

FIG. 4 depicts an embodiment of the socket of the prosthesis, by which the length of the socket can be varied;

FIG. 5 is a sectional view of the illustration according to FIG. 4, along sectional line V-V; and FIG. 6 illustrates a variant of a leg prosthesis including an inflatable shaped body.

Figure 1:
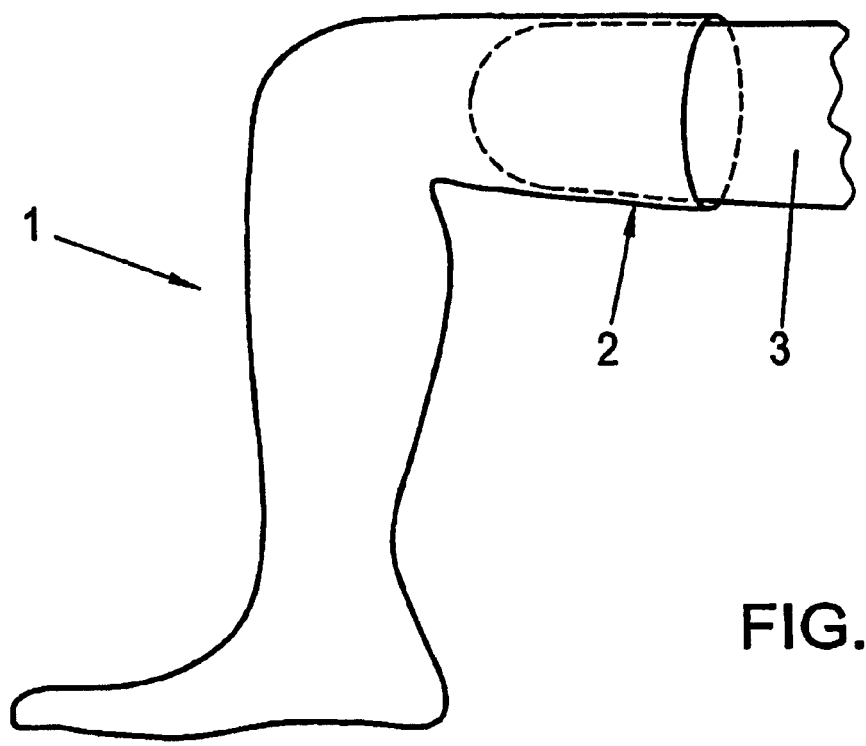
FIG. 1 is a schematic side view of a leg prosthesis according to the present invention.

FIG. 1 schematically illustrates a prosthesis for the optical substitution of a missing limb, namely a missing leg in the example illustrated, which comprises a shaped body 1 for replacing the missing limb and a socket 2 for connecting the prosthesis to the stump 3 of the missing limb. In accordance with the invention, the shaped body 1 is made of a synthetic material and does not fulfill any functional needs. This means that no walking or gripping function can be carried out by the aid of the present prosthesis. Furthermore, the periphery of the socket 2 for connecting the prosthesis to the stump 3 is variable such that the prosthesis can be adapted to missing limb stumps of different sizes.

Figures 2, 3:
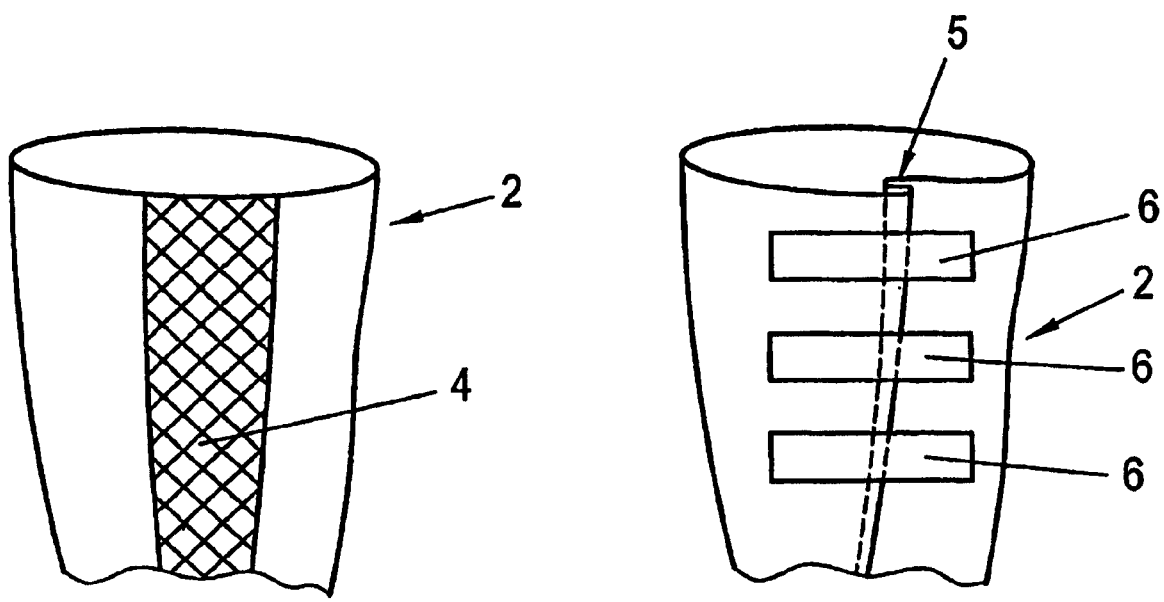
FIG. 2 shows a partial region of the socket of the prosthesis including an elastic partial region.
FIG. 3 illustrates the socket of the prosthesis including quick-acting closures.

FIG. 2 depicts an alternative embodiment of the variability of the circumference of the socket 2, which consists in a partial region 4 of the socket 2 being made of elastic material. The periphery of the socket 2 is, thus, adaptable to differently large stumps 3 of missing limbs within a certain range.

Another variant of the variability of the periphery of the socket 2 is illustrated in FIG. 3, where the circumference of the socket 2 can be fixed by the aid of quick-acting closures 6 and, for instance, Velcro fasteners. To this end, the socket 2 is, for instance, laid in two pleats in the region 5, with the pleat being fixed by means of quick-acting closures 6. In this manner, the rapid and simple connection of the prosthesis to the stump 3 of the missing limb even of elderly patients can be achieved.

FIGS. 4 and 5 illustrate a variant embodiment according to which the socket 2 is variable also in terms of length. This is achieved in that the socket, at least over a partial region of its length, is made of an elastic material and forms at least one pleat 7, which is again fixed by means of quick-acting closures and, in particular, Velcro fasteners.

Finally, FIG. 6 is a sectional view of a variant embodiment of the prosthesis, wherein the shaped body 1 is made of an elastic, air-tight synthetic material 9 and comprises at least one valve 10 for inflating the shaped body 1. Thus, an inflatable prosthesis is provided, which is particularly simple and cost-effective to produce. On sensitive sites, reinforcement layers 11 of synthetic material may be arranged on the inner side of the shaped body 1. In addition, fastening strips 12 may be provided to further secure the prosthesis to the patient's body.

Although the drawings are exclusively directed to leg prostheses, arm prostheses may as well be produced in accordance with the present invention.

The invention claimed is:

1. A light prosthesis as a visual substitute for a missing limb, comprising:
   a shaped body (1) for replacing the missing limb comprises a socket (2) for connecting the prosthesis to a stump (3) of the missing limb, wherein the shaped body (1) is made of a light synthetic material, and that the periphery of the socket (2) for connecting the prosthesis to the stump (3) is variable, the length of the socket (2) is variable and the socket (2) is made of an elastic material at least over a partial region of its length, and that the elastic material forms at least one pleat (7) in the partial region to achieve a change in the length of the socket (2), wherein the at least one pleat (7) is fixed by quick-acting closures (8) comprising a Velcro fastener and wherein the prosthesis is a cosmetic non-structural visual substitute for a missing limb.

2. The light prosthesis of claim 1, wherein the shaped body (1) includes a joint or several joints to replace the joint(s) of the missing limb.

3. The light prosthesis of claim 1, wherein the prosthesis comprises one or more interconnected air chambers.

4. The light prosthesis of claim 1, wherein the prosthesis comprises coloration that mimics skin.

5. The light prosthesis of claim 1, wherein the prosthesis is non functional.

6. The light prosthesis of claim 1, wherein the prosthesis is molded in the shape of at least a portion of an arm or a leg.

7. The light prosthesis of claim 1, wherein the prosthesis comprises a valve for inflating the light prosthesis.

* * * * *